United States Patent [19]

Studer

[11] 4,025,306
[45] May 24, 1977

[54] PROCESS AND APPARATUS FOR HEARTWORM MICROFILARIAE DETECTION

[76] Inventor: Arnold David Studer, Box 5, West Grove, Pa. 19390

[22] Filed: Aug. 16, 1976

[21] Appl. No.: 714,445

[52] U.S. Cl. .............................. 23/230 B; 23/259; 128/2 F; 128/2 G; 195/103.5 R; 195/127

[51] Int. Cl.² .................... G01N 33/16; G01N 1/30

[58] Field of Search ............... 23/230 B, 259, 292; 195/103.5 R, 127; 128/2 F, 2 G; 424/11

[56] References Cited

UNITED STATES PATENTS

| | | | |
|---|---|---|---|
| 3,463,322 | 8/1969 | Gerade | 210/455 |
| 3,874,851 | 4/1975 | Wilkins et al. | 23/230 B |

*Primary Examiner*—R.E. Serwin

*Attorney, Agent, or Firm*—Rollin D. Morse

[57] ABSTRACT

Methods and apparatus are already in use in the field of veterinary medicine for detecting microfilariae of heartworm in blood, comprising lysing blood samples to destroy corpuscular components, filtering the lysed samples on microporous transparent filters, staining any microfilariae on the filter, and observing the stained microfilariae under a microscope. The present invention simplifies and improves upon the older practices by providing a premix of lysing solution and staining dye, in a disposable vial, and a disposable filtrate vial surmounted by disposable filter cap holding a microporous filter element. The blood sample is injected into the premix for simultaneous lysing and staining, transferred to the filter cap for filtration and the filter element transferred to a microscope slide for observation.

9 Claims, 5 Drawing Figures

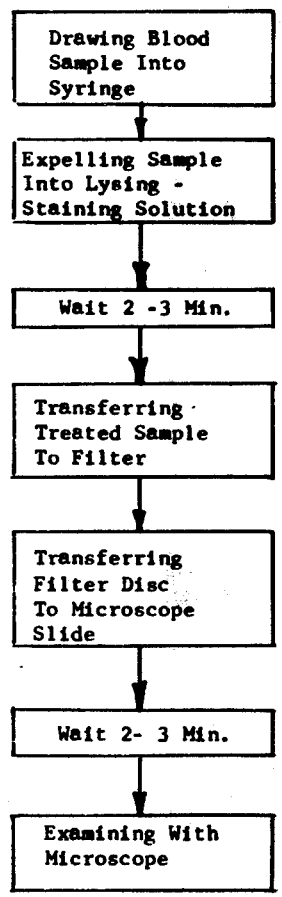
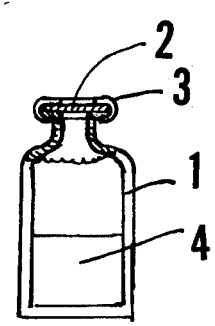
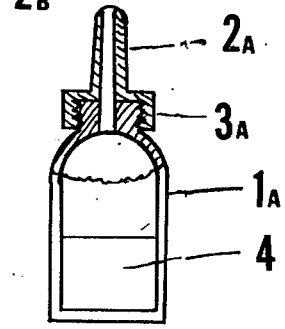
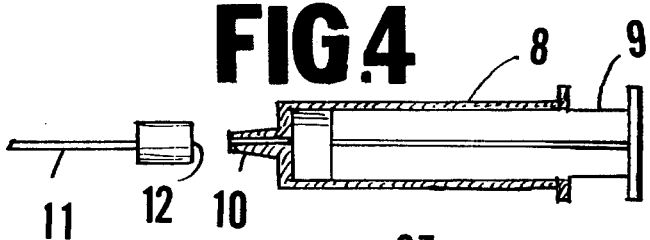
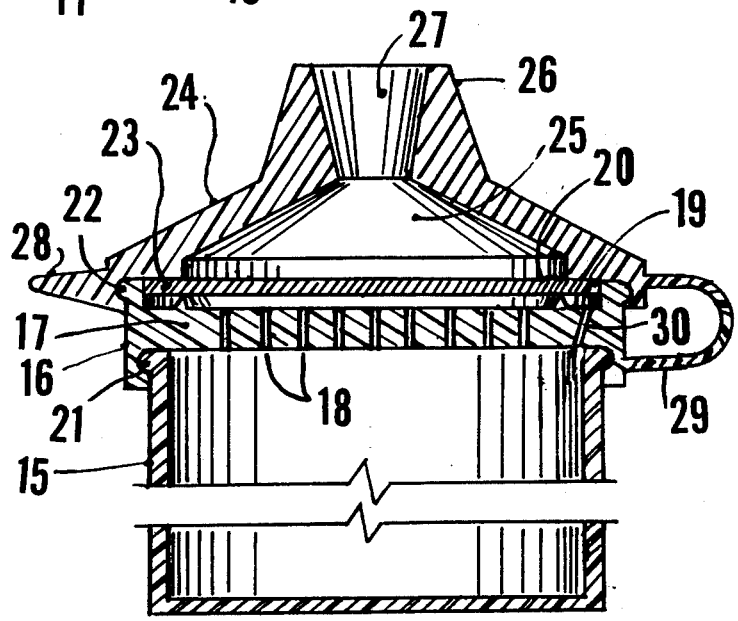

PROCESS AND APPARATUS FOR HEARTWORM MICROFILARIAE DETECTION

INTRODUCTION

The present invention relates to the detection of microfilariae in blood.

It has been known for some time that microfilariae of heartworm, as found in veterinary practise especially in dogs, may be detected in samples of the blood of the affected animal, by first breaking down the cellular and corpuscular components of the blood, the breakdown being affected by mixing the blood with lysing materials which do not affect the microfilariae, staining them with a dye on the filter, and then observing the microfilariae under a microscope. The concentration of microfilariae observed is a measure of the seriousness of the infestation. Such a method is descirbed in "Veterinary Clinical Pathology" by E. V. Coles, published in 1967 by W. B. Saundars Company, Philadelphia.

A modified procedure is described in U.S. Pat. No. 3,874,851, issued Apr. 4, 1975 to R. J. Wilkins et al. A principal aspect of the modification is the use of the syringe with which the blood sample was drawn as a reaction vessel for the lysis by drawing lysis solution from reservior into the sample of blood within the syringe. After lysis is complete, the syringe contents is expelled onto a filter, and after filtration, is stained as cited in the Cole reference.

Among the difficulties with the earlier methods is the possibility of contaminating the reservoir of lysis solution with blood. Another problem is the number of sequential operations that must be carried out.

The present invention has for its objects the overcoming of the above mentioned difficulties and problems, and the provision of inexpensive, single-use disposable apparatus elements, whereby not only is the likelihood of valid testing increased, but the cost per test is decreased. A simplified and altered procedure is an objective.

SUMMARY STATEMENT

These objects and others are achieved by a process and apparatus as explained in the following specification. In particular, the method of the invention is an improved process for the detection of microfilariae in blood, comprising in combination, a. the preparation of a solution mixture containing at least one dye suitable for staining said microfilariae, and components suitable for causing lysis of the blood, said dye and said components being mutually compatible,
  b. adding a blood sample to said solution mixture and holding briefly to allow lysis of the blood and staining of said microfilariae to take place,
  c. filtering the lysed stained sample on a microporous filter pad, and
  d. transferring the filter pad to a microscope slide for examination for stained microfilariae.

The aforesaid process, in which said blood sample
  a. previously obtained by drawing into a syringe,
  b. is ejected into said solution mixture, and
  c. after having been held briefly the stained lysed sample is transferred for filtration on said microporous filter.

The aforesaid process, in which the said blood sample
  a. previously obtained by drawing into a syringe with needle,
  b. is ejected through said needle into said solution mixture,
  c. after having been held briefly the stained, lysed sample is withdrawn through said needle into said syringe and
  d. is then ejected from said syringe for filtration on said microporous filter.

The aforesaid process, in which the solution mixture comprises aqueous formaldehyde of 0.5 – 5% strength by weight, together with a staining dye for microfilariae stable in formaldehyde. The said staining dye may be at least one of gentian violet, methylene blue, trypan blue, or bromcresol purple, or any other chemically compatible dye which will afford a good staining of the microfilariae.

The aforesaid process in which the solution mixture is employed in about 1 to 5 times the volume of the blood sample.

The invention comprises also an apparatus for carrying out the detection of microfilariae in a blood sample, in cooperative combination, comprising a. a standard hypodermic syringe with a male end coupling with the female end of a hypodermic needle, for drawing a sample of blood from an animal under test,
  b. a first vial containing a solution mixture of dye suitable for staining said microfilariae, together with components suitable for causing lysis of the blood, said due and said cmponents being mutually compatible, said first vial having a cover means, penetrable by said needle
  c. a second vial for receiving a filtrate
  d. a filter-media-holding cover for said second vial, operable to facilitate removal of said filter media, and having an inlet means
  e. said inlet means being adapted to enable transfer of fluid without leaking, from said first vial to said filter-media-holding cover.

In particular, the inlet to the filter-media-holding cover may have a female taper adapted to cooperate with the male end of the hypodermic needle. Alternatively, the first vial's cover means may have a male protrusion adapted to cooperate with the female taper of the inlet to the filer-media-holding cover.

Preferably, the filter-media-holding cover is shaped to be irremovably snapped in place on said second vial, but has a closure readily opened to enable transfer of the filter media to the microscope. The vial may also be formed integral with the cover.

FIGURES

FIG. 1 shows in diagrammatic form, the sequence of operations of the process of this invention.

FIG. 2 shows a vial containing premixed lying solution and staining dye.

FIG. 3 shows an alternative premix vial.

FIG. 4 shows a syringe with its hollow needle.

FIG. 5 shows a filter-topped filtrate vial.

DESCRIPTION

Two alternate processes will be described. Both are the same as to the broad process steps given in FIG. 1, but slightly different as to detail.

The first process uses the apparatus of FIGS. 2, 4 and 5 in combination, whereas the second substitutes the apparatus of FIG. 3 for that of FIG. 2.

It will facilitate the overall understanding, first to explain the apparatus, and then to explain the functions and process.

FIG. 2 depicts a small vial, designated 1, with a cover 2, and a cover reainer 3, and containing a lysing-staining solution 4. The vial may conveniently be of standard commerical construction as used in the pharmaceutical industry for containing vaccines or other liquids to be injected. Commonly such vials are of plastic or glass, plastic being preferred for the present invention because of the ready disposablility by burning, and the very low cost. A capacity of a few milliliters, more specifically 2 – 5 milliliters, is preferred for 1 milliter blood sample.

The vial has a cover 2, of a soft, self-sealing, rubber-like materal, in the form of a disc, held in place on the mouth of the vial by an aluminum tubular retainer which is rolled or crimped around the mouth of the vial and the cover to make a liquid-tight seal. The cover 2, is soft enough and thin enough to be penetrated by a hypodermic needle, and yet to reseal when the needle is removed.

FIG. 4 depicts a standard hypodermic syringe 8 with mating hollow needle 11, and plunger 9. The needle has a base 11 with a female taper 12 that mates removably with a male taper on the syringe tip 10. Preferably the syringe and plunger are of plastic construction for ready disposability by burning.

FIG. 5 shows a filter vial 15 with a specially fabricated filter cap having a multiply-perforated cover 17, and a filter closure 24. Conveniently the filter vial 15 can be a commerical cylindrical vial of plastic with a slightly beaded upper edge at 21. A capacity slightly greater than the capacity of vial 1 is adequate for a single-use filter, the preferred form of this invention. More specifically, a capacity of 10 milliliters is adequate in the preferred form.

The cap 16 has an edge enclosing tightly, preferably irremovably, the bead 21. Its cover part 17 is perforated with many small holes 18, and may be grooved or serrated on its upper face, whereby a filter disc placed on this face is supported aginst fluid pressure, but passageways on and through the cover 17 are provided, for flow of the filtrate. The upper face of cover 17, is also provided with an annular raised edge 20, of triangular cross section and sharp upper edge. The outer periphery of 16 is provided with a beaded edge 22, onto which may be snapped (but in this part, removably rather than irremovably) the filter closure 24, adapted on its under side to contain and press down upon the edge of a filter disc 23, whereby solution to be filtered cannot leak past the edges of the disc. Above the central region of the disc, the closure has a generally frusto-conical distribution chamber 25, connected at its smaller end with an inlet 27, extending through boss 26. The inlet 27 is preferably a conical hole adapted to couple with the male end 10 of the hypodermic syringe 8 (in the first alternative) or with the male conical end of the closure 2a of vial 1a (in the second alternative).

Both the cap 16 and its closure 24 may preferably be made of plastic such as polyethylene or polypropylene, and may be formed together in one piece, connected by hinge 29; for ready opening to remove the filter disc, a tab 28 may be provided, on the side of the closure opposite to the hinge. In addition to the holes 18 in the cover 17, a vent hole 30 should be provided near one edge, and so located that excess pressure of air in the vial will be vented to the atmosphere, whereby to facilitate filtration.

The microporous filter disc is preferably a clear or at least translucent disc of microporous plastic such as General Electric "Nucleopore" polycarbonate film with pores of about 8 micron diameter, or a similar "Millipore" material whereby stained microfilariae retained on the disc may be reasily viewed under a microscope at about 100 diameters.

The staining and lysis solution 4 contained in the first vial 1, or 1a, may be of various compositions, both as to stain, and as to lysing component. It has been found that formaldehyde in water solution, at a concentration in the range of 0.5 to 5.0%, preferably about 4% with a staining dye component such as gentian violet, methylene blue, trypan blue, Bromcresol purple, Wright's Blood Stain, are particularly effective in causing both lysing of the blood, and staining of the microfilariae, and the components are mutually compatible.

The vial 1a shown in FIG. 3 is an alternative to that shown in FIG. 2. Its closure includes a retainer 3A and a snout 2A, the snout having an exterior taper adapted to mate with the female tapered inlet 27 of filter vial 15. The snout has a bore slightly larger than the hypodermic needle's outside diameter. Preferably, this bore extends form the inner end of the snout almost to the outer end, leaving at the tip a wall so thin as to be easily penetrated by the hypodermic needle. Alternatively, the bore may pass completely through the snout, and be closed at the outer end with a plastic friction-fit cap 2B.

As a preferred system for sale to veterenarians in ready-to-use packaged form, the following cooperative components would be provided:

a. Disposable hypodermic syringe and needle,
b. Sealed lysing-staining vial containing the premeasured lysing-staining solution,
c. Filter vial capped with its snapped-on filter cap, with microporous filter in place. All components of this single-use package are readily disposable by incineration as commonly practised in connection with medical and veterinary laboratories.

In use, the veterinary or assistant would open the aforesaid package, assemble the hypodermic syringe and needle, draw a sample of bood form the animal, inject this sample into the lysing-staining vial (either through the rubber closure of alternative 1 in FIG. 2, or through the plastic tip closure of snout 2A, in FIG. 3).

The injected blood is mixed with the lysing-staining solution in the vial 1 or 1a by shaking. The needle (and syringe) may be left in place in the vial of alternative 1, FIG. 2. In the vial of FIG. 3, the needle and syringe may be disconnected and tossed into the disposal hooper.

After a few minutes of lysing and staining, the mixture is transferred to the filter. For alternative 1, the transfer is effected by up-ending the lysing-staining vial 1, drawing the syringe and needle back nearly to the point of withdrawal from closure 2, and then drawing back plunger 9 of the syringe, whereby to suck out the mixture from the vial.

Thereupon, the needle is removed from the syringe and tossed to disposal, together with the vial, and the syringe tip 10 is inserted into the conical coupling inlet 27 of the filter cap on filter vial 15. With the syringe tip down, the plunger is pushed in, to force the mixture out of the syringe, through the filter disc 23, into vial 15. The plunger 9 may be partially withdrawn, to suck air into the syringe, and then this air expelled through the filter disc to ensure full expulsion of the filtrate. The syringe is withdrawn and tossed to disposal. A water wash step is desirably included as a part of the filtration step.

Filter closure 24 is next opended (by lifting tab 28) and with forceps the microporousfilter disc 23 is lifted out and transferred to a microscope slide glass. A cover glass is applied, and the slide placed upon the stage, and inspected at 100 diameters magnification. If microfilariae were present they will have absorbed stain, and will have become considerably straighter than their normal shape, as a side benefit form the lysing treatment. The individual microfilariae will be readily visible in the microscope, extending across as much as one-quarter of the field of view.

Once the filter is lifted out, the filtrate vial and its filter cover are also tossed to disposal.

Returning to the second alternative shown in FIG. 3, after injection of the blood, the syringe and needle are withdrawn, and disposed of. After the sort holding time for lysis and staining to take place, the vial 1A is upended and its tip 2A inserted into the conical inlet coupling 27 of the filter vial. By squeezing the vial 1A, its contents is expelled through the filter disc 23 into vial 15. A second squeeze drives air through the disc, to expel the last of the liquid.

The vial is detached from coupling 27, and disposed of. The filter disc is then removed and treated as already described.

Consideration emphasis has been placed in the foregoing description on an apparatus that is completely disposable, and which would be used only once. it will be apparent, however, that each apparatus element could be reused if preferred. For example, several vials, sufficient for a day's analyses, could be filled form pipettes connected to reservoirs of dye solution, lysing solution, or premixed lysing-staining solution. Syringes and needles could be washed and reused, as was formerly the common practise. And filter vials could be dumped, washed, and reused. However, such reuse brings in possibilities of contamination, and of obtaining incorrect results, and, while within the scope of the appended Claims, is not a preferred process of the invention.

Trials of the foregoing apparatus and processes have demonstrated an interesting sidelight, namely, that immediately after transfer of the filter pad to the microscope slide, the stain within the microfilariae is rather pale, and completely absent from the rest of the field; but, after several minutes wait, the color of the microfilariae darkens, and they become much more readily observable, even through all surplus stain had been washed away from the surrounding field.

What I claim is

1. An improved process for the detection of microfilariae in blood, comprising in combination,
    a. the preparation of a solution mixture containing at least one dye suitable for staining said microfilariae, and components suitable for causing lysis of the blood, said dye and said components being mutually compatible,
    b. adding a blood sample to said solution mixture and holding briefly to allow lysis to take place and staining of said microfilariae,
    c. filtering the stained, lysed sample on a microporous filter and
    d. transferring the filter to a microscope slide for examination for stained microfilariae.
2. The process of claim 1, in which the said blood sample
    a. previously obtained by drawing into a syringe,
    b. is ejected into said solution mixture, and
    c. after having been held briefly the stained lysed sample is transferred for filtration on said microporous filter,
3. The process of claim 1, in which the said blood sample
    a. previously obtained by drawing into a syringe with needle,
    b. is ejected through said needle into said solution mixture,
    c. after having been held briefly the stained, lysed sample is withdrawn through said needle into said syringe and
    d. is then ejected from said syringe for filtration on said microporous filter,
4. The process of claim 1, in which the solution mixture comprises aqueous formaldehyde of 0.5–5% strength by weight, together with a staining dye for microfilariae stable in formaldehyde.
5. The process of claim 4, in which said staining dye is at least one of gentian violet, methylene blue, trypan blue, or bromcresol purple.
6. the process of claim 1, in which the solution mixture is employed in about 1 to 5 times the volume of the blood sample.
7. An apparatus for carrying out the detection of microfilariae in a blood sample, comprising in cooperative combination
    a. a standard hypodermic syringe with male end and a needle with female socket for drawing sample of blood from an animal under test,
    b. a first vial containing a solution mixture of dye suitable for staining said microfilariae, together with components suitable for causing lysis of the blood, said dye and said components being mutually compatible, said first vial having a cover means,
    c. a second vial for receiving a filtrate
    d. a filter-media-holding cover for said second vial, operable to facilitate removal of said filter media, and haivng an inlet.
    e. said inlet being adapted to enable transfer of any fluid without leaking from said first vial to said filter media-holding cover.
8. The apparatus as in claim 7, in which the said inlet means has a female taper adapted to cooperate with the male end of the hypodermic syringe.
9. The apparatus of claim 7, in which the cover means of the first vial has a male protrusion adapted to cooperate with a female taper of the inlet of the said filter-media-holding cover.

* * * * *